United States Patent [19]

Ryder

[11] Patent Number: 4,579,823

[45] Date of Patent: Apr. 1, 1986

[54] STERILIZATION INDICATOR

[75] Inventor: Francis E. Ryder, Arab, Ala.

[73] Assignee: Ryder International Corporation, Arab, Ala.

[21] Appl. No.: 536,290

[22] Filed: Sep. 27, 1983

[51] Int. Cl.⁴ .................. C12M 1/24; C12Q 1/22; G09F 9/00; B65D 25/54

[52] U.S. Cl. ................. 435/296; 116/307; 215/228; 215/230; 215/253; 215/307; 220/366; 435/31; 435/810

[58] Field of Search ............... 435/31, 291, 296, 311, 435/810; 436/1; 426/231; 116/212, 312, 315, 307; 215/230, 250, 253, 228, 307, 344, 365, DIG. 1; 422/102; 251/343–345, 350; 220/366

[56] References Cited

U.S. PATENT DOCUMENTS

| | | |
|---|---|---|
| 2,961,108 | 11/1960 | Johnson ............................ 215/228 |
| 3,216,600 | 11/1965 | Dreps ............................... 215/230 |
| 3,440,144 | 4/1969 | Andersen ....................... 195/103.5 |
| 3,638,918 | 1/1972 | Denholtz ............................ 259/48 |
| 3,655,035 | 4/1972 | Muhlbauer ........................ 206/47 |
| 3,661,717 | 5/1972 | Nelson .......................... 195/103.5 |
| 3,739,947 | 6/1973 | Baumann et al. ................. 222/136 |
| 3,762,540 | 10/1973 | Baumann et al. ................. 206/47 |
| 3,809,280 | 5/1974 | Park et al. ................... 220/366 X |
| 4,291,122 | 9/1981 | Orelski ................................ 435/31 |
| 4,304,869 | 12/1981 | Dyke ................................ 435/296 |
| 4,355,111 | 10/1982 | Shimizu et al. ................. 435/243 |
| 4,461,837 | 7/1984 | Karle et al. ..................... 435/296 |

Primary Examiner—Robert J. Warden
Assistant Examiner—P. Kate White
Attorney, Agent, or Firm—Trexler, Bushnell & Wolters, Ltd.

[57] ABSTRACT

A sterilization indicator device comprises a receptacle for containing a spore disc and a sealed ampule of culture medium. A closure is threaded onto the receptacle and cooperates with the receptacle to provide a passageway for the sterilization gases to reach the spore disc. Upon completion of the sterilization, the closure is threaded further onto the receptacle to fracture the ampule and cause the nutrient to come into contact with the spore disc. At the same time an indicator flag is moved from an initial position to a second position to indicate that the device has been activated. Also, a seal is provided between the closure and the receptacle to seal off the spore disc from exposure to ambient air during incubation of the spore strip.

8 Claims, 9 Drawing Figures

STERILIZATION INDICATOR

BACKGROUND OF THE INVENTION

The device of the present invention relates to a biological indicator for sterilization processes.

In order to test the effectiveness of a steam or gas sterilization process, standardized spores of a bacterial strain sufficiently resistant to the sterilization medium are placed on a carrier, such as a spore disc or strip, and the strip is exposed to the sterilization medium being tested, normally gas, steam or dry heat. A proper sterilization of a standardized spore strain insures sterilization of the bacterial strain in the chamber of the autoclave or other sterilization device. On the other hand, the presence or survival of these standardized spore strains indicates an unsatisfactory sterilization process.

After the sterilization process has been completed, the survival of the spores is determined by mixing a test solution containing a culture or growth medium and a pH indicator with the bacterial spores and thereafter incubating the culture for growth. In spore fermentation, for example, glucose contained in the growth medium is utilized by viable or living spores, and pyruvic acid is produced as a byproduct. The pyruvic acid lowers the pH of the test solution and results in a change of color of the pH indicator in the solution. If there are no living or viable spores following sterilization, the pH and the color of the test solution remains essentially unchanged.

Various ways are known for mixing the test solution with the strips containing the microorganisms or spores. One such way consists of providing a hermetically sealed glass ampule containing the culture medium and enclosing the ampule and the test strip in a container and providing a means to crush the ampule whereby the culture medium floods the test strip in the container. Thereafter, the saturated test strip in the container is incubated for the requisite period of time in order to determine whether or not viable bacteria is present. Devices of the foregoing type are shown, for example, in U.S. Pat. Nos. 3,440,144; 3,661,717 and 4,304,869.

The present invention is an improvement on devices of the foregoing type in that the device of the present invention is relatively inexpensive to fabricate, is reliable in operation, and has other conveniences and features not found in the prior art.

OBJECTS AND SUMMARY OF THE INVENTION

An object of this invention is to provide a sterilization indicator device which is relatively easy to use and provides a clear indication as to whether or not the sterilization process has been satisfactory or not.

A further object of this invention is to provide a device of the type stated in which the spore disc is isolated from ambient air during the incubation period and wherein the device is provided with means for indicating that a seal has been provided to seal off ambient air from contact with the spore disc.

A further object of this invention is to provide a device of the type stated in which the fractured glass particles of the ampule are effectively prevented from interfering with the flow of nutrient to the spore disc.

In accordance with the foregoing objects, the device comprises a receptacle having a chamber and an opening into the chamber, a source of microorganisms within said chamber, a frangible closed ampule of liquid culture medium in said chamber, a closure for said opening and having a first position in which said closure has a part thereof juxtaposed with said ampule, said closure having a second position in which said closure engages and fractures said ampule to release the culture medium into contact with said source of microorganisms and moves said flag to a second position, cooperating means on said receptacle and closure for permitting relative movement of said receptacle and closure to shift said closure from its first position to its second position, means providing passageway means for the flow of sterilization medium from the exterior of the device to said source of microorganisms when the closure is in its first position, cooperating means on said closure and receptacle forming a gas tight seal for said passageway means when the closure is in its second position to isolate said microorganism source from external contamination and to retain said closure in its second position, and means by which the source of microorganisms may be observed from the exterior of the device.

In an illustrated form of the invention, an indicator flag is attached to the receptacle by two tabs, one of said tabs being fracturable by the closure when the closure moves from its first position to its second position and the other of said tabs constituting a hinge at which the flag deflects to the second position thereof. The illustrated form of the invention also employs a novel, reliable seal arrangement and a shield internally of the chamber to prevent any ampule particles from interfering with the sealing action once the ampule is fractured.

DETAILED DESCRIPTION

Figure 1:
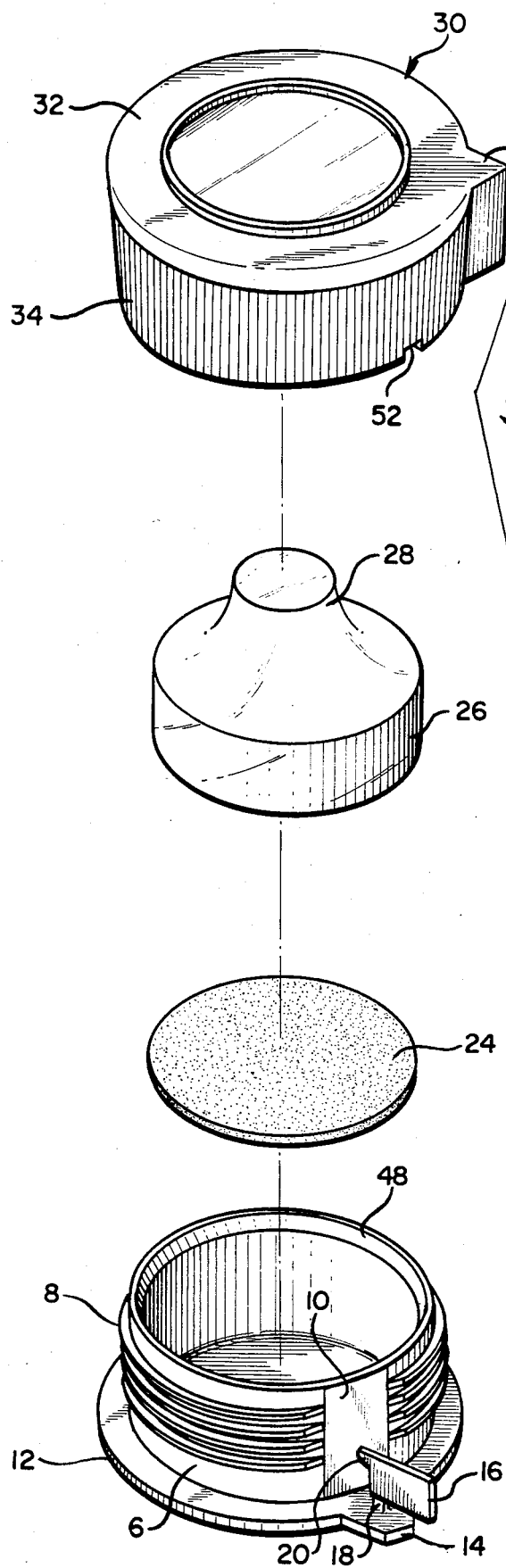
FIG. 1 is an exploded perspective view of a sterilization indicating device constructed in accordance with and embodying the present invention.

Referring now in more detail to the drawings, there is shown a sterilization indicating device 1 comprising a receptacle 2 which is formed of a one-piece molded plastic material such as a polycarbonate resin. The receptacle 2 includes a bottom wall or base 4 and a surrounding sidewall 6. The sidewall 6 is formed with an external thread 8 which is interrupted at two zones 10,10 one hundred eighty degrees apart and at which the sidewall 6 may be flattened, for purposes presently more fully appearing.

An annular flange 12 projects radially outwardly of the junction of the bottom wall 4 and sidewall 6, and the flange 12 includes a further radial projection 14 in the region of one of the zones 10,10.

An indicator flag 16 is attached to the receptacle 2 by two tabs 18, 20. The tab 20 secures a corner of the flag 16 to the sidewall 6 in the zone 10 while the tab 18 attaches another corner of the flag 16 to the projection 14.

The bottom and sidewall 4, 6 of the receptacle 2 cooperate to form a chamber 22 for receiving a biological spore disc 24 which is disposed against the bottom wall 4. The spore disc 24 is of known composition and-/or construction and includes a standardized strain. For example, if the indicator is intended for use in ethylene oxide sterilization, the strain might be *Bacillus subtilis*. If the indicator device is for use in steam sterilization, *Bacillus stearothermophilus* may be the strain that is used. Also within the chamber 22 is a frangible glass ampule 26 which seats against the spore disc 24 and which has a plateau portion 28 that projects upwardly beyond the rim of the sidewall 6. The ampule 26 is hermetically sealed and contains a suitable test solution of known composition. For example, the test solution may be a nutrient media, such as trypticase soy broth, and a pH indicator such as phenol red which is an alkaline indicator that changes color to yellow upon contact with acid.

Provided for cooperation with the receptacle 2 is a closure cap 30 which, like the receptacle 2, may be a transparent, one-piece member of polycarbonate resin. The closure 30 is formed with an end wall 32 and a surrounding cylindrical sidewall 34, the latter having an internal thread 36 that mates with the thread 8. The inner surface 38 of end wall 32 is of arcuate configuration whereby the end wall 32 is thickest at its center. When the cap and closure are assembled, the surface 38 is in close proximity with the adjacent surface of the ampule plateau 28. The arcuate surface 38 tends to make the end wall 32 a lens that magnifies the view of the interior of the chamber 22.

Figure 4:
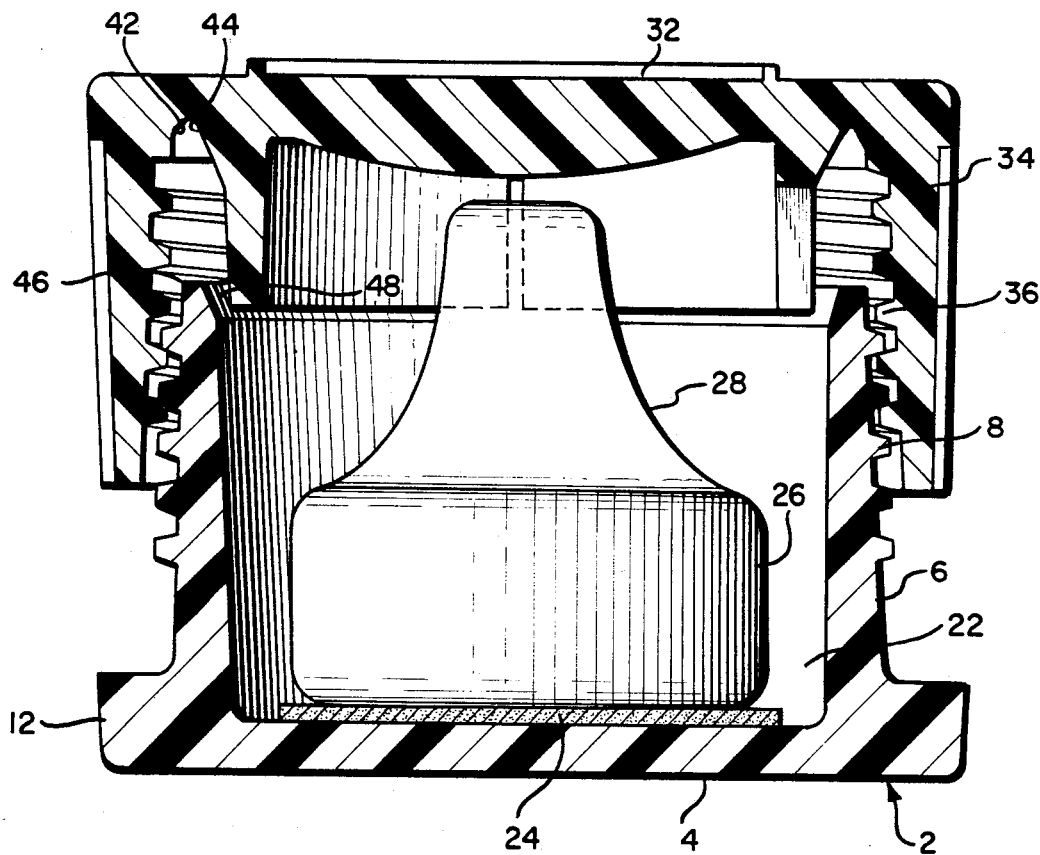
FIG. 4 is an enlarged sectional view taken along line 4—4 of FIG. 2.
Figure 5:
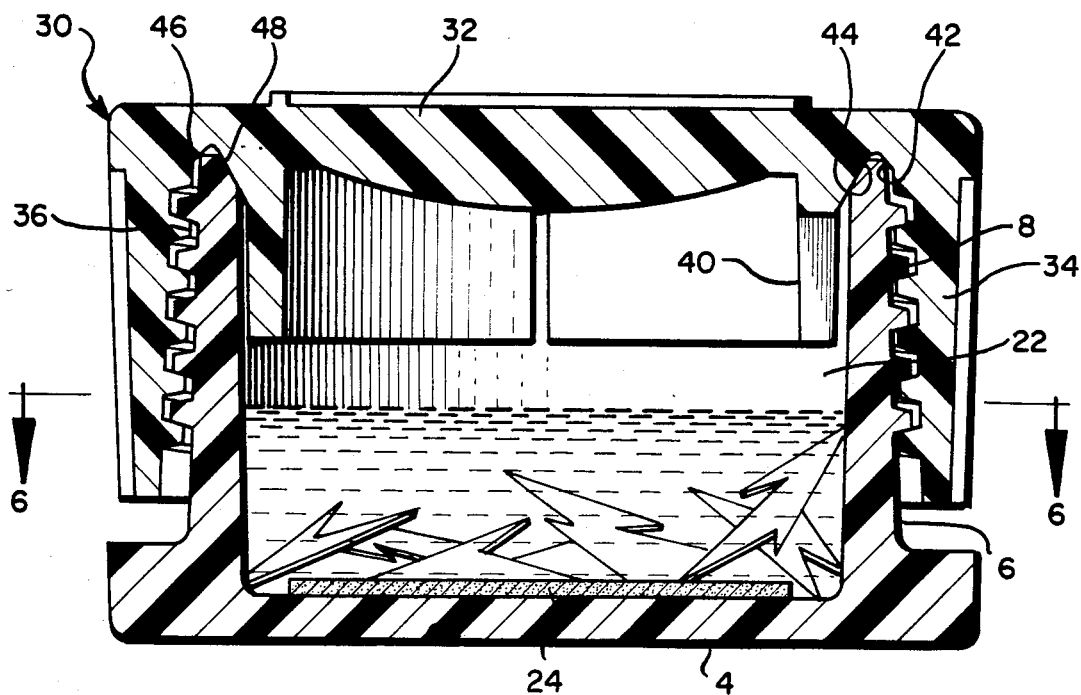
FIG. 5 is a sectional view similar to FIG. 4 but showing the device after the ampule therein has been fractured to expose the culture medium to the microorganism-containing disc.
Figure 6:
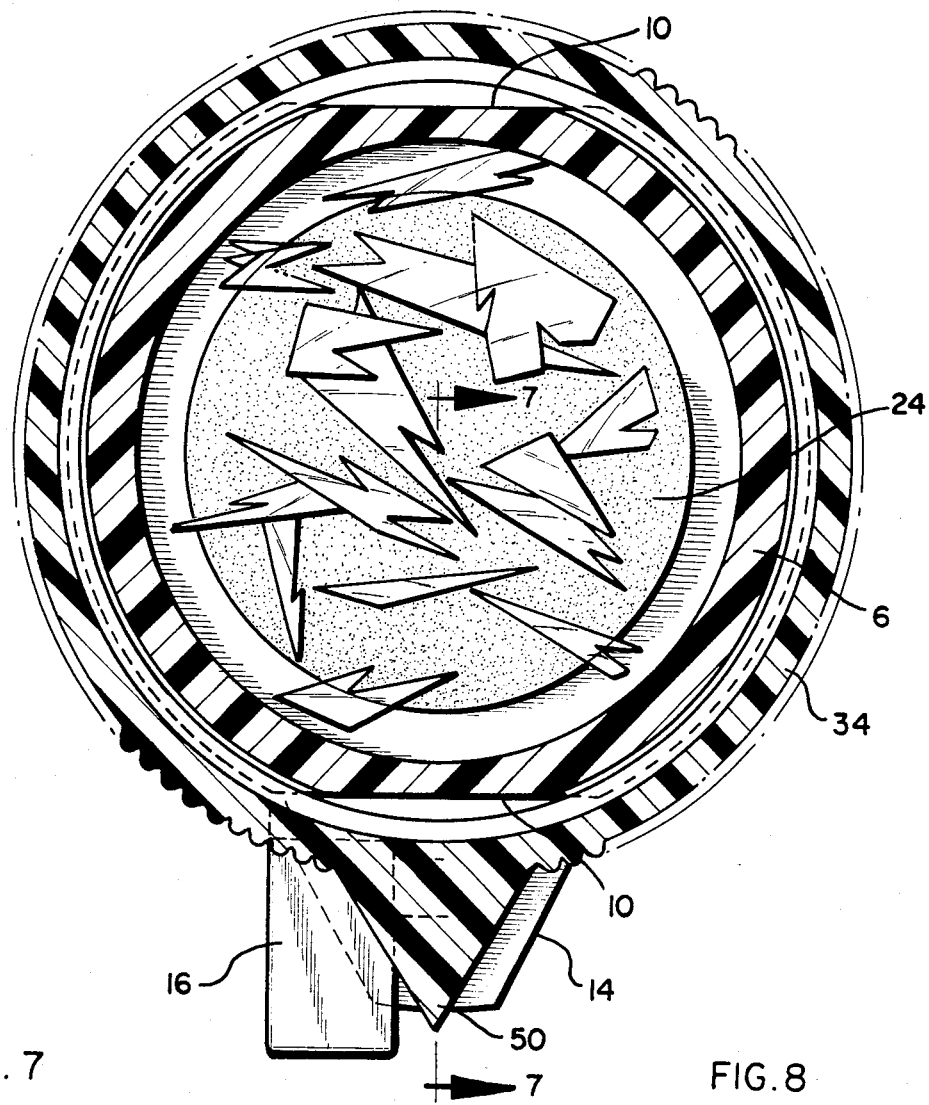
FIG. 6 is a sectional view taken along line 6—6 of FIG. 5.
Figure 7:
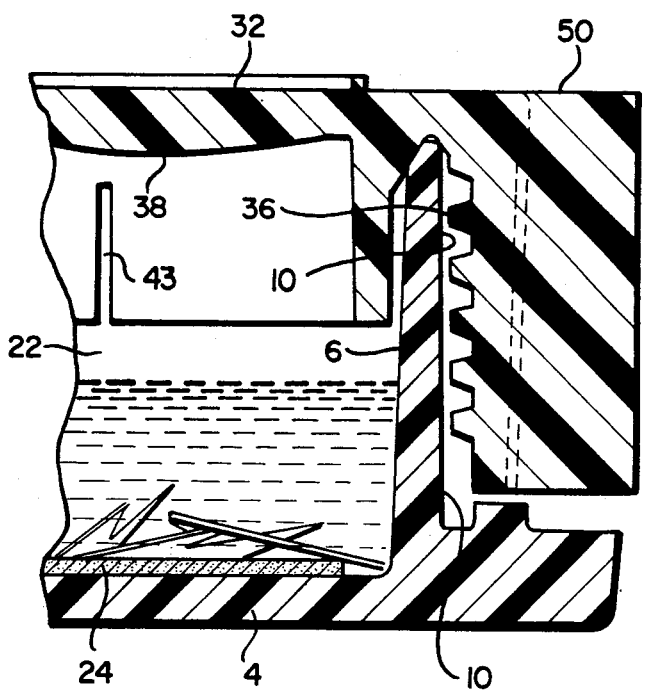
FIG. 7 is a fragmentary sectional view taken along line 7—7 of FIG. 6.

Projecting axially from the inside of the end wall 32 is an internal skirt 40 having one or more longitudinal vent slots 43. The skirt 40 is positioned to lie radially outwardly of the ampule 26 and radially inwardly of the receptacle sidewall 6. At the junction of the skirt 40 and the sidewall 34, the closure 30 is formed with adjacent opposed conical, wedge surfaces 42, 44 which, as best seen in FIGS. 4 and 5, are adapted to engage, the rim of the sidewall 6 to provide a peripheral seal. In this regard, the rim of the sidewall 6 includes an outer edge 46 and an inner conical surface 48 which engage respectively the wedge surfaces 42 and 44 to attain the aforementioned peripheral seal.

Integrally provided on the external surface of the sidewall 34 is a generally triangular indicator projection 50 which is normally circumferentially offset from the flag 16. Also formed on the sidewall 34 at the rim thereof is a notch 52 (FIGS. 1-3) which receives the upper end of the indicator flag 16.

In assembling the components of the indicator and with the spore disc 24 and the ampule 26 within the receptacle 2, the cap or closure 30 may be axially pushed without rotation onto the receptacle, the threads 8, 36 yielding elastically to permit such relative movement of the closure and receptacle. Alternatively, the closure may be threaded partially onto the receptacle and then axially shifted without rotation to snap past a thread turn. In any case, in the final relative axial movement during assembly of the closure and receptacle, the notch 52 is lined up circumferentially with the flag 16 whereby the engagement of the flag 16 in the notch 52 serves initially to limit relative axial movement of the closure and receptacle during the assembly process. Thereafter, the interengagement of the flag 16 and the notch 52 serves to prevent accidental significant rotation of the closure relative to the receptacle.

Figure 2:
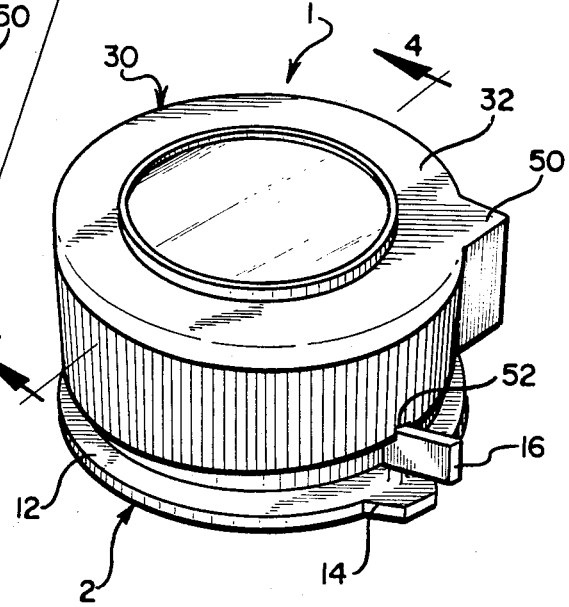
FIG. 2 is a perspective view of the device in a condition for disposition in a sterilization medium with a batch to be sterilized.
Figure 3:
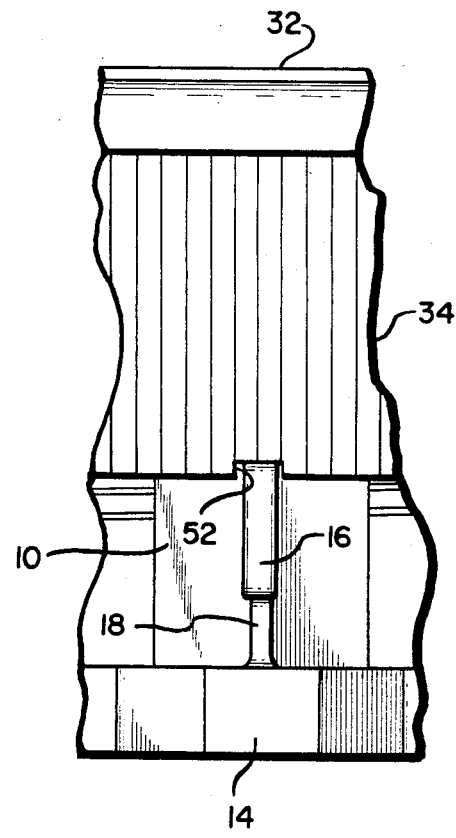
FIG. 3 is an enlarged fragmentary elevational view of a portion of the device in the region of the indicator flag.
Figure 8:
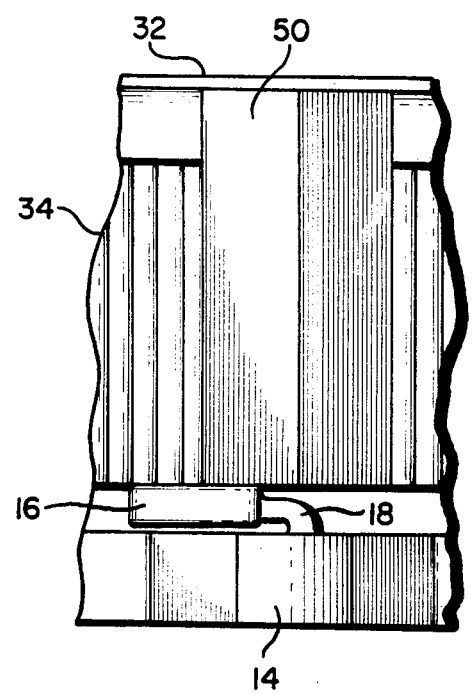
FIG. 8 is a fragmentary elevational view similar to FIG. 3 but with the device in the condition shown in FIG. 7.

In use the device 1, when in the condition shown in FIGS. 2-4, is placed in the sterilizer along with the other items to be sterilized. During the sterilization process, the sterilizing medium will flow through the passageways at the zones 10,10 and into the chamber 22. Upon removal of the device 1 from the sterilizer the cap is immediately turned relative to the receptacle to shatter the ampule 26 whereupon the cap will be shifted to the position shown in FIGS. 5-8. As can be appreciated, movement from the position as shown in FIG. 4 to that as illustrated in FIG. 5 will bring the end wall 32 into engagement with the ampule 26, compressing said ampule and causing it to fracture or shatter. The culture medium will flow into the chamber 22 and contact the spore disc 24. Also, the engagement of the closure sidewall 34 with the indicator flag 16 will cause the tab 20 to rupture and result in the indicator flag being bent downwardly, as shown in FIG. 8, about a hinge formed by the tab 18, thereby indicating that the device has been activated. The engagement of the edge 46 with the conical surfaces 42 and 44 produces a wedged engagement that serves to form a tight seal across the passageways at the zones 10,10 and also about the entire periphery of the edge or rim 46, thereby to seal the chamber 22 from the influence of ambient air and possible contamination subsequent to sterilization during the following incubation procedure. At the same time, the wedging engagement of the surfaces 42, 44 and 46, 48 tends to lock the closure and receptacle in the positions shown in FIG. 5, thereby preventing unthreading of the closure. Furthermore, the alignment of the projection 50 with the projection 14 will indicate that the passageways at the zones 10 have been sealed off, as set forth above.

The internal skirt 40 serves an important function in that it shields the sealing zone or surface at 42, 44, 46 and 48 from glass particles resulting from rupture or fracture of the ampule 26. In order to assure proper fracture of ampule 26, the glass from which it is constructed is quite brittle and will shatter upon fracture. As such, there is a danger that glass particles will lodge on the sealing surfaces 42, 44, 46 or 48 and prevent attainment of the desired wedged, sealed engagement. The shield 40 serves to deflect all glass particles interiorly of the chamber and preserves the sealing action.

The vent slot or slots 43 also serve an important purpose. In this regard, if these slots were not present, it is possible that air might be trapped within the skirt 40, which could force the culture medium from the ruptured ampule 26 upwardly and past the rim or edge 46 before a seal is attained. The slot or slots 43 serve to vent air to the atmosphere prior to sealing of the chambers 22 and passageways 10, 10.

The sealed unit is now placed in an incubator for a period of about seven days to observe further growth and fermentation of viable bacteria. If viable bacteria spores are present, they will ferment the glucose in the nutrient medium to produce pyruvic acid, thereby lowering the pH of the solution and causing the phenol red to change from red to yellow. A color change indicates an unsatisfactory sterilization process. If the solution remains red, a negative test result is obtained and a satisfactory sterilization is indicated.

Figure 9:
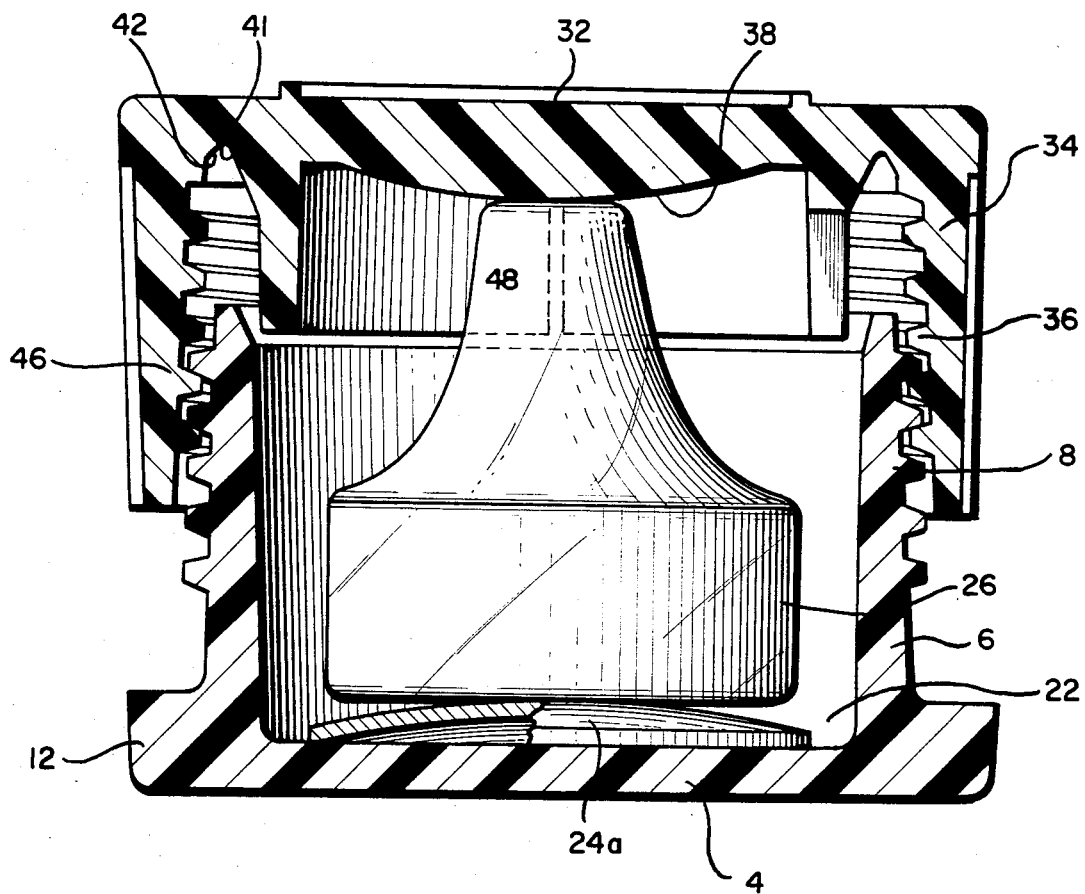
FIG. 9 is a view similar to FIG. 4, but illustrating a modified form of the indicator device of the invention.

FIG. 9 illustrates a slightly modified form of the indicator device of the present invention. In this embodiment, the construction of the receptacle 2 and closure cap 30 remains unchanged, the primary difference being that the spore disc 24a is of a bowed or dome shaped configuration. Toward this end, the modified spore disc 24a is fabricated from a relatively stiff, yet resilient paper material, such that it will maintain its bowed or dome-like shape, and if flexed will return to its original configuration. Various paper materials are commercially available from which the spore disc 24a may be constructed, which will yield the desired structural properties, as detailed herein.

More specifically, the resilient paper material used for the spore disc 24a, and the domed configuration are selected such that in the pre-assembled, pre-tested condition of FIG. 9, the spore disc will support the ampule 26 in engagement with the inner convexed surface 38 of the closure end wall 32. The resilient nature of the dome shaped spore disc 24a serves as a biasing or spring means to maintain this engagement. Also, the resilient nature of the domed shaped disc 24a permits slight movement of the ampule 26 relative to the closure 30, while maintaining the above discussed engagement. The disc 24a thus serves a further purpose in that it functions as a shock absorber that reduces relative movement of the ampule 26 during handling, packaging and shipment of the assembled indicator 1. Thus, with the design of FIG. 9, the chances that the ampule 26 may become damaged or permanently ruptured are materially reduced by use of the dome shaped spore disc 24a.

Accordingly, there has been illustrated and described herein two preferred forms of the present invention. It is envisioned that those skilled in the art may devise various alternative designs or modifications, once possessed with a disclosure of the present invention. Insofar as such alternative designs or modifications are encompassed by the claims appended hereto, they are deemed to fall within the spirit and scope of the present invention as defined by said claims.

I claim:

1. A sterilization indicator device comprising: a receptacle having a chamber and an opening into the chamber, said chamber being capable of receiving therein a source of microorganisms and a frangible closed ampule containing a liquid culture medium, a closure member for said receptacle opening; a plurality of cooperatingly engaged thread turns on said receptacle and said closure for permitting said closure to be engaged upon said receptacle in a first, initial position and also permitting movement of said closure from said first, initial position to a second position, such that movement from said first position to said second position will cause said closure to engage and fracture said ampule to release the culture medium for contact with the source of microorganisms, a portion of the cooperatingly engaged thread turns on said receptacle being interrupted for the entire axial extent of the thread turns at at least one location, to provide a passageway across the thread turns to said receptacle chamber from the exterior of said indicator device, such that a sterilization medium may flow from the exterior of said indicator device into said chamber for exposure to said source of microoganisms when the closure is in its first position, cooperating means on said closure and receptacle for forming a gaseous tight seal between said closure and said receptacle when said closure is moved to said second position to isolate said microorganism source from external contamination.

2. A sterilization indicator device according to claim 1 wherein indicating means are provided on said receptacle, which will assume a first orientation when said closure is in said first position, and will be deformed to a second orientation upon movement of said closure to said second position.

3. A sterilization indicator device according to claim 1, wherein indicating means are included for indicating when said closure member is in said first position or said second position, said indicating means comprising a projection on said receptacle extending radially outward from an exterior wall surface thereof, a detent formed in said closure member for receiving said projection when said closure member is in said first position, the engagement thereof preventing both axial and rotative movement of the closure with respect to said receptacle, said projection being deformable to permit movement of said closure member from said first position to said second position with the deformation thereof providing an indication of said movement.

4. A sterilization indicator device according to claim 1, wherein said closure includes an end wall and axially extending sidewalls, and said closure being formed of a transparent material with said end wall including a curved surface to provide a lens that magnifies the view of the chamber.

5. A sterilization indicator device according to claim 1, wherein said closure includes an end wall and a cylindrical sidewall extending axially thereof, and a skirt that projects from said end wall and is disposed radially inward of said sidewall and is adapted to substantially surround said ampule such that upon fracture of said ampule, said skirt will contain any shattered glass particles and prevent them from interfering with said cooperating means for forming the gaseous tight seal.

6. A sterilization indicator device according to claim 1, wherein said cooperating means on said closure and said receptacle surfaces on said closure member, a peripheral rim on said receptacle member that is received in wedge sealed engagement between said opposed tapered surfaces to provide said gaseous tight seal.

7. A sterilization indicator device comprising; a receptacle having a chamber and an opening into the chamber; a source of microorganisms disposed within said chamber, a frangible closed ampule of liquid culture medium positioned in said chamber, a closure member for said receptacle opening; a plurality of cooperatingly engaged thread turns on said receptacle and said closure member, responsively; such closure member being formed of a resilient material such that ssid closure member may be disposed upon said receptacle by relative axial movement without rotation, the thread on said closure member yielding elastically to snap past the thread turns on said receptcle without rotation thereof, until said closure is received in a first, initial position, said closure being moveable to a second position by rotation thereof which movement will cause said closure member to engage and fracture said ampule to release the culture medium into contact with said source of microorganisms; a portion of the engaged said thread turns on the receptacle being interrupted for the entire axial extent thereof at at least one location thereby providing a passageway across said thread turns for the flow of sterilization medium from the exterior of the indicator device into said chamber for exposure to said source of microorganisms when said closure is in its first initial position; and sealing means on said closure and receptacle forming, a fluid and gaseous tight seal across said passageway means when the closure is in its second position, thereby isolating said microorganism source from external contamination; and indicator projection on said receptacle extending radially outwardly from the wall thereof; a detent formed in said closure member for receiving said projection upon movement of said closure member to said initial position, with the engagement of said projection in said detent preventing inadvertent movement of the closure member from said first position to said second position and upon intended movement to said second position, said projection providing an indication of said movement by deformation thereof.

8. A sterilization indicator device according to claim 7, wherein said closure member includes an end wall and an axially extending sidewall, a skirt member extending from said end wall and being disposed radially inwardly of said sidewall, said skirt surrounding said ampule such that upon fracture thereof said skirt will prevent any glass particles from interfering with the operation of said sealing means.

* * * * *

UNITED STATES PATENT AND TRADEMARK OFFICE
CERTIFICATE OF CORRECTION

PATENT NO. : 4,579,823
DATED : April 1, 1986
INVENTOR(S) : Francis E. Ryder

It is certified that error appears in the above-identified patent and that said Letters Patent is hereby corrected as shown below:

Column 6, line 46, please insert between "receptacle" and "surfaces" the words --for forming a gaseous tight seal includes opposed tapered--.

Column 6, line 57, change "responsively; such" to --respectivey; said--.

Signed and Sealed this

Nineteenth Day of August 1986

[SEAL]

Attest:

DONALD J. QUIGG

Attesting Officer

Commissioner of Patents and Trademarks